United States Patent [19]

Balana et al.

[11] 4,086,135

[45] Apr. 25, 1978

[54] PROCESS FOR STEPPING GRAIN AND PRODUCTS OBTAINED THEREFROM

[75] Inventors: Ramon Cairo Balana; Antonio Montserrat Caixes, both of Barcelona, Spain

[73] Assignee: CPC International Inc., Englewood Cliffs, N.J.

[21] Appl. No.: 533,393

[22] Filed: Dec. 16, 1974

[30] Foreign Application Priority Data

Dec. 14, 1973 Spain .................................. 421.472

[51] Int. Cl.$^2$ ............................................... C12B 1/00
[52] U.S. Cl. ......................................... 195/17; 127/68
[58] Field of Search ............................ 195/17, 20–25; 127/67, 68, 71; 426/18, 44, 49, 52, 507, 618

[56] References Cited

U.S. PATENT DOCUMENTS 3,597,274  8/1971  Gillenwater et al. .................. 127/68

3,677,897  7/1972  Jeffreys .................................. 426/49

FOREIGN PATENT DOCUMENTS 1,912,088  8/1970  Germany .............................. 127/68

OTHER PUBLICATIONS

Whistler et al., "Starch: Chemistry & Technology", Academic Press, vol. II, pp. 32–38.

*Primary Examiner*—R. B. Penland
*Attorney, Agent, or Firm*—John P. Floyd; John A. Stemwedel; David H. LeRoy

[57] ABSTRACT

A process for steeping grain wherein the steepwater is inoculated with an inoculum containing a microorganism of the genus Lactobacillus at or near the beginning of the steeping process. The process reduces the steeping time and increases the content of lactic acid in the steepwater. The process also reduces the amount of sulfur dioxide needed in the steeping process.

8 Claims, No Drawings

PROCESS FOR STEPPING GRAIN AND PRODUCTS OBTAINED THEREFROM

BACKGROUND OF THE INVENTION (a) Field of the Invention

This invention relates to an improvement in the wet milling process for separating and recovering the various constituents (primarily starch, gluten and oil) from cereal grains, the two cereal grains most commonly processed by means of the wet milling process being corn and "milo", also known as grain sorghum (the scientific name being Sorghum vulgare, of the family Gramineae). More specifically, the present invention relates to an improvement in the steeping step of the wet milling process, whereby the steeping step is considerably shorter than in the conventional process and the lactic acid content of the steep water is increased.

(b) Description of The Prior Art

The wet milling process is an old and well known industrial process, and is fully described in the published literature. For detailed information on the process, reference may be made, for example, to either of the following two publications: (1) the chapter entitled "Starch", by Stanley M. Parmerter, contained in Volume 18 of Kirk-Othmer, Encyclopedia of Chemical Technology, Second Edition, Interscience Publishers, a division of John Wiley & Sons, Inc., New York, London, Sidney, Toronto (1969), and (2) the chapter entitled "Manufacture of Corn and Milo Starches" by Stanley A Watson, appearing in Starch: Chemistry and Technology, Volume II Industrial Aspects, edited by Roy L. Whistler and Eugene S. Paschall, Academic Press, New York and London (1967).

In the manufacture of starch by means of the wet-milling process the grain, after preliminary cleaning to remove foreign material, is almost invariably steeped for a period of about 36 to 60 hours (most commonly, for a period of from 40 to 50 hours) in warm acidulated water at about 50° C, having a concentration of sulphur dioxide of about 0.15%. Parameters which have a positive effect on the grain steeping step of the corn wet milling process are: concentration of sulphur dioxide, steeping temperature and time. With the increased disintegration of the protein network the endospern is softened and the water penetration in the grain is achieved. It is well known in the art that during the steeping process the protein network swells and tends to form a large number of swollen globules of hydrated proteins.

As the conditions during steeping, (i.e., temperature, pH, and soluble carbohydrates) are favorable for the development of lactic acid bacteria, they grow at a very fast rate adsorbing and eliminating other microorganisms. The opinion that the formed lactic acid influenced the protein degradation has proven to be erroneous. Also the addition of acids, including lactic acid does not appear to improve the steeping process anymore than distilled water.

SUMMARY OF THE INVENTION

The present invention relates to an improved process for steeping grain in the wet-milling process for producing starch, comprising; steeping grain in steepwater which has been inoculated with an inoculum of a microorganism of the genus Lactobacillus. The steepwater is preferably inoculated with the inoculum of the microorganism at or beginning of the steeping process to thereby reduce the steeping time and increase the amount of lactic acid formed in the steepwater effluent. By the use of steepwater which has been inoculated with an inoculum of a microorganism of the genus Lactobacillus, the steeping time can be reduced from 40 to 60 hours to about 25 hours.

The process of the invention also produces a steepwater effluent from the steeping step having more than 20 percent, dry basis, lactic acid.

The inoculum containing the microorganism may be derived from any suitable species of Lactobacillus. The *Lactobacillus delbruckii* and *Lactobacillus leichmanii* are preferred. These are well known microorganisms which have been described in the literature, see for example, "Industrial Microbiology", Prescott et al, pp. 305–307 (1959).

The use of the inoculated steepwater in the steeping step also makes it possible to operate the steeping step at lower temperatures than previously i.e., possible, i.e. temperatures as low as about 45° C. The content of sulfur dioxide at the beginning of the steeping process can be from about 0.075% to about 0.1%, whereas in steeping processes of the prior art as much as 0.15% or more sulfur dioxide has been required.

The quality of the starch obtained by the practice of the present invention is at least equal or improved from the standpoint of purity and viscosity to the prior art steeping processes, and the yield of the starch is at least equal to the starch obtained by the prior art processes.

DESCRIPTION OF THE PREFERRED EMBODIMENTS

The steeping process of the invention is conducted in a manner such that the steepwater contains a high percentage of dry substance. The steeping tanks are mounted in a series of 6 to 13 steep tanks. The flow of water is counter current to the flow of corn. This results in a steepwater (also known as light steepwater) of 5 to 7% of dry substance or about 63 grams per liter or about 4° Baume'. The light steepwater can be subsequently concentrated to about 50% dry substance for further use and/or sale.

The steeping process of the present invention is preferably conducted over a period of 23 to about 26 hours. The temperature at which the steeping is conducted by the use of steepwater inoculated with an inoculum containing a microorganism of the genus Lactobacillus will generally fall within the range of from about 45° C to about 50° C, however, it is possible to conduct the steeping process at temperatures as low as about 40° C or as high as 55° C. However, at these extreme temperatures, variations in the condition of the starch product and/or the other processing variables may have to be taken into consideration. The initial sulfur dioxide concentration in the steeping process of the present invention is generally in the range of from about 0.075% to about 0.1%, however, a higher concentration of sulfur dioxide may be employed, e.g., concentrations as high as 0.15%. For each ton of corn processed and steeped in accordance with the practice of the present invention, 1.4 to about 1.8 $M^3$ of sulfur dioxide water is added and 0.7 to about 0.9 $M^3$ of light steep water is drained from the system.

The production of Lactobacillus preparations useful in the practice of the present invention is a well known procedure in the fermentation industry. In commercial practice, it is recommended to proceed by stages. These stages may be few or many, depending on the nature of the process and the characteristics of the microorganisms. Ordinarily, propagation is started by inoculating a nutrient medium (generally Agar) and maintaining the original culture at suitable temperatures for a period of several days. This step or stage is repeated one or more times in flask or vessels containing the same or larger volumes of nutrient medium. These stages may be conveniently referred to as culture development stages. The microorganisms, with or without accompanying culture medium, from the last development stage, commonly referred to as the seed stage, are introduced or inoculated into a large-scale fermentor to produce commercial quantities of the inoculum to be used for the steepting process of the invention.

The reasons for growing the Lactobacillus microorganism in stages are many-fold, but are primarly dependent upon the conditions necessary for the growth of the microorganisms. These conditions include stability of the microorganisms, proper nutrients, pH, osmotic relationships, temperature and maintenance of fewer culture conditions during fermentation.

The following is an example of preparing the inoculum to be used in the practice of the invention.

A pure freeze-dryed culture of *Lactobacillus leichmanii* (obtained from the University of Salamanca) was incubated in 20 ml of Agar for 20 hours at 37° C. (this original culture can be stored as a stock culture for about 20 days at 10° C. for further use as an original culture medium for subsequent development stages). A first culture was prepared by inoculating 20 ml of the original culture per 20 ml of Agar medium and incubating the same for 20 hours at 37° C. (this first culture medium can be stored as a stock culture for further use for about one week at 10° C). A second culture was then prepared by inoculating 3 ml of the first culture per 300 ml of Agar and incubating the same for 20 hours at 37° C. (this second culture can be stored as a stock culture for further development stages for about one week at 10° C). The third culture development was prepared by incubating 40 ml per 40 liters of culture medium of the second culture stage and incubating the same for 24 hours at 40° to 45° C. (this third culture development can be stored for further use for 24 hours at 10° C).

In Table 1 herein below the specific components of the culture medium for each of the development stages described above is set forth.

TABLE 1

| COMPONENTS | I$^a$ | II$^2$ | III$^3$ |
|---|---|---|---|
| Agar | 16 g | — | — |
| Peptone | 10 g. | 16 g. | 600 g. |
| Meatextract | 10 g. | — | — |
| Yeast Extract | 10 g. | 15 g. | 600 g. |
| Dextrose | 20 g. | 20 g. | 2000 g. |
| Tween "60" | 1 ml | 1 ml | — |
| Dipotassium Phosphate | 2 g. | 2 g. | 6 g. |
| Diammonium Citrate | 2 g. | 2 g. | 6 g. |
| Magnesium Sulphate 7H$_2$O | 0.2 g. | 0.2 g. | 8 g. |
| Magnesium Sulphate 4 H$_2$O | 0.05 g. | 0.05 g. | — |
| Ammonium Carbonate | 2 g. | 2 g. | 200 g. |
| Calcium Carbonate | — | — | 1000 g. |
| Manganese Sulphate | — | — | 4 g. |
| Water Until | 1 L (Distilled) | 1 L (Distilled) | 40 L |

$^a$Original culture (medium-broth)
$^b$First and second culture (medium-broth)
$^c$Third culture (medium-broth)

In the practice of the invention 40 liters of the third culture stage is employed for each 68 tons of corn.

In one example of practicing the process of the invention, a battery of eleven (11) steep tanks are arranged in series. The flow of water is counter current to the flow of the corn in the steep tanks. The water used for steeping the corn is inoculated with the Lactobacillus culture inoculum produced according to the procedure described above (i.e., 40 liters of the inoculum is used for each 68 tons of corn). The tanks are designated as Nos. 2 to 12. Corn filling occurs in tank No. 3 and the steepwater runs through tank Nos. 2 to 12. The steepwater from tank No. 12 goes to tank No. 2 and then to the light steepwater drain. In this example, the inoculum or culture produced by the procedure described above is introduced into tank No. 5, the same tank the sulfur dioxide is added. The steeping time is 25 hours and 68 tons of corn are processed. The light steepwater from the drain is about 700 to 900 liters per ton of corn. The steeped corn leaves the No. 4 tank to be grinded at a grind rate of 550 tons of corn per day. The amount of sulfur dioxide containing water added in tank No. 5 is 75 M$^3$ and the amount of light steepwater drained is 75 M$^3$. In this particular example the draining of the light steepwater averages from 700 to 900 liters per ton of corn.

The invention is illustrated further by the following examples which, however, are not to be taken as limiting in any respect. All parts and percentages, unless expressly stated to be otherwise, are by weight.

EXAMPLE 1

This example describes a steeping operation conducted under the conditions described previously and the effect of the new process on the end products.

A corn wet milling plant having a daily grinding capacity of 550 tons of commercial corn is equipped with 11 steeps and 68 tons of commercial corn each. Each steep is ground in about 3 hours. One of the 11 steeps is then filled with 68 tons of commercial corn having a moisture content of 14.8%. (in this experiment yellow corn No. 3 was used). 40 liters of a culture of *Lactobacillus Delbruckii* (University of Salamanca as prepared in the above description) was added to this steep. The contact time of the *Lactobacillus Delbruckii* culture inoculum with the steep corn was about 38 hours. This operation is repeated ten times so that in the end there was no interference from the previous normal steeping process, where no inoculum containing the Lactobacillus addition was conducted. The general conditions during the steeping process were:

TABLE II

| Conditions | New Process | Old Process |
|---|---|---|
| Time (Hours) | 40 | 40 |
| Temperature | 49° C | 51° C |
| Sulfur Dioxide % | 0.15% | 0.15% |
| Lactobacillus addition | Yes | No |

The light steepwater had the following analysis:

TABLE III

| Component Analyzed | New Process | Old Process |
|---|---|---|
| Baume | 3.6° | 3.6° |
| Sulfur dioxide, % | 0.0144% | 0.0144% |
| Lactic Acid (% Dry base) | 22% | 18% |
| Reducing Sugars (% Dry base) | 1.7% | 6.5% |

The addition of the inoculum containing *Lactobacillus delbruckii* clearly has a positive effect on the steeping by increasing the final lactic acid content in the light steepwater effluent. There is a parallel decrease in the content of the reducing sugars. Thus, by the practice of the present invention one is able to obtain more than 20% lactic acid in the light steepwater effluent from the steeping process of the invention.

EXAMPLE 2

This example demonstrates that the steeping time can be reduced by the use of an inoculum containing a microorganism of the genus Lactobacillus. The conditions employed in this example are identical to those described in Example 1 except that the steeping time was reduced to 30 hours. The general conditions during the steeping are described in the following table.

TABLE IV

| Conditions | New Process | Old Process |
| --- | --- | --- |
| Time (Hours) | 30 | 40 |
| Temperature (° C) | 49° C | 49° C |
| Sulfur dioxide, % | 0.0150% | 0.0144% |

The light steepwater had the following analysis:

TABLE V

| Component Analyzed | New Process | Old Process |
| --- | --- | --- |
| Baume | 4.0 | 3.6 |
| Sulfur dioxide, % | 0.0150% | 0.0144% |
| Lactic Acid (% Dry basis) | 21.8% | 18% |
| Reducing sugar (% Dry basis) | 1.9% | 6.5% |

It is clearly evident from the data in this example that by the addition of an inoculum containing a culture of *Lactobacillus delbruckii* it is possible to reduce the steeping time. This reduction did not affect the final content of lactic acids, as compared with a 40 hour steeping operation (Example 1). The reduction in the steeping time only resulted in a minor sacrifice in the yield of lactic acid, i.e., the amount of lactic acid formed was 21.8% as compared to 22% when 40 hours of steeping time is utilized.

EXAMPLE 3

In this example, the general procedure described above in Examples 1 and 2 and the previously description for preparing the inoculum were employed. The inoculum was prepared from a microorganism of the species *Lactobacillus leichmanii* (No. 287 supplied by the University of Salamanca, Spain). The steeping time was reduced to 24 hours. The amount of sulfur dioxide used was 0.08 to 0.1% and the temperature was reduced to 45° C. In parallel to this experiment, 10 steeping operations were conducted, wherein the time was reduced to 24 hours. In these comparison experiments, the sulfur dioxide was not reduced and a *Lactobacillus leichmanii* culture inoculum not added. These 10 operations are referred to hereinbelow as the "Control". The results of these experiments are set forth in the following table.

TABLE VI

| Conditions | New Process | Control | Old Process |
| --- | --- | --- | --- |
| Time (Hours) | 24 | 24 | 40 |
| Temperature | 45° C | 50° C | 51° C |
| Sulfur dioxide, % | 0.09% | 0.15% | 0.15% |

The light steepwater had the following analysis:

TABLE VII

| Component Analyzed | New Process | Control | Old Process |
| --- | --- | --- | --- |
| Baume | 3.6 | 4.2 | 3.6 |
| Sulfur dioxide, % | 0.013% | 0.015% | 0.015% |
| Lactic acid (% DB) | 25.3% | 14% | 18% |
| Reducing sugars | 3.4% | 11.3% | 6.5% |

This example clearly exemplifies the fact that the inoculation of the steepwater with a culture of *Lactobacillus leichmanii* increases the final lactic acid content in the light steepwater, and that this higher yield is achieved in a shorter period of time. This example also illustrates the fact that reduced amounts of sulfur dioxide can be employed as compared to the prior art processes.

EXAMPLE 4

In this example the light steepwater effluent was further inoculated with Lactobacillii cultures and incubated for 24 hours. It was then possible to achieve 22% or more of lactic acid which is the minimum amount required for further antibiotic fermentation. A comparison to this process called "Normal Process + Incubation" with the new process can be done as follows:

TABLE VIII

| | New Process | Normal + Incubation |
| --- | --- | --- |
| Time (Hours) steeping | 24 | 40 |
| Time (Hours) incubation | 0 | 24 |
| Time (Hours) total | 24 | 64 |
| Lactobacillus addition | | |
| - steeping | yes | no |
| - incubation | — | yes |
| Temperature ° C | | |
| - steeping | 45° C | 50° C |
| - incubation | — | 40° C |
| SO$_2$ | 0.08% | 0.15% |

This example clearly demonstrates that the addition of *Lactobacillus leichmanii* at the beginning of the steeping process achieves better results as far as yield in lactic acid is concerned than the normal process even followed by an incubation step in a considerably shorter period of time, but that the latter modification results in an amount of reducing sugars which still makes it superior to the Normal process.

While the invention has been described in connection with specific embodiments thereof, it will be understood that it is capable of further modification, and this application is intended to cover any variations, uses, or adaptions of the invention following, in general, the principles of the invention and including such departures from the present disclosure as come within known or customary practice in the art to which the invention pertains and as may be applied to the essential features hereinbefore set forth, as fall within the scope of the invention.

We claim:

1. In the process of steeping grain in warm acidulated water at the beginning of the wet milling process for the separation and recovery of the various components of the grain, the improvement comprising adding an inoculum of a microorganism of the genus Lactobacillus to the warm acidulated water in which the grain is steeped.

2. The process of claim 1, wherein the water for the steeping is acidulated by the addition thereto of sulfur dioxide in an amount of from about 0.075% to about 0.1%.

3. The process of claim 1, wherein said steeping process is conducted at a temperature in the range of from about 45° C to about 50° C.

4. The process of claim 1, wherein the steeping process is terminated when the content of lactic acid in the steepwater reaches about 20%, by weight, dry substance basis.

5. The process of claim 1, wherein said inoculum is derived from a microorganism selected from the group consisting of *Lactobacillus delbruckii* and *Lactobacillus leichmanii*.

6. The process of claim 1, wherein the inoculum is added to the steepwater at or near the beginning of the steeping process.

7. The process of claim 1, wherein said steeping process is conducted for a period of from about 23 to about 26 hours.

8. The process of claim 1, wherein the steeping process is terminated when the content of lactic acid in the steepwater reaches about 22%, by weight, dry substance basis.

* * * * *